United States Patent
Scorsin et al.

(10) Patent No.: US 10,779,935 B2
(45) Date of Patent: Sep. 22, 2020

(54) CARDIAC STENT-VALVE AND DELIVERY DEVICE FOR SUCH A VALVE

(71) Applicant: Epygon, Paris (FR)

(72) Inventors: Marcio Scorsin, Curitiba (BR); Enrico Pasquino, Savigny (CH); Marco Gard, Borgomasino (IT); Claudio Piccoli, Piverone (IT)

(73) Assignee: Epygon, Paris (FR)

( * ) Notice: Subject to any disclaimer, the term of this patent is extended or adjusted under 35 U.S.C. 154(b) by 327 days.

(21) Appl. No.: 15/122,642

(22) PCT Filed: Feb. 26, 2015

(86) PCT No.: PCT/EP2015/054057
§ 371 (c)(1),
(2) Date: Aug. 31, 2016

(87) PCT Pub. No.: WO2015/135763
PCT Pub. Date: Sep. 17, 2015

(65) Prior Publication Data
US 2017/0065409 A1 Mar. 9, 2017

(30) Foreign Application Priority Data
Mar. 11, 2014 (EP) .................................. 14305355

(51) Int. Cl.
*A61F 2/24* (2006.01)
(52) U.S. Cl.
CPC .............. *A61F 2/2418* (2013.01); *A61F 2/24* (2013.01); *A61F 2/2412* (2013.01);
(Continued)
(58) Field of Classification Search
CPC ............ A61F 2/24; A61F 2/2409–2418; A61F 2250/0039
See application file for complete search history.

(56) References Cited

U.S. PATENT DOCUMENTS 4,759,758 A * 7/1988 Gabbay ................. A61F 2/2412
623/2.13
4,960,424 A 10/1990 Grooters
(Continued)

FOREIGN PATENT DOCUMENTS

CN 1596090 3/2005
CN 101262833 9/2006
(Continued)

OTHER PUBLICATIONS

Definition of Point, Math Open Reference, pp. 1-3, date accessed Nov. 10, 2018.*
(Continued)

*Primary Examiner* — Rebecca S Preston
(74) *Attorney, Agent, or Firm* — Andre Roland S.A.; Nikolaus Schibli (57) ABSTRACT

A cardiac stent-valve (1), preferably a mitral stent-valve, comprising a stent component (2) and a valve component (3), wherein the stent component (2) comprises an inflow end (4) and an outflow end (5) and a wall between the inflow (4) and the outflow end (5), and wherein the valve component (3) is made of one single leaflet (6); the periphery of said single leaflet (6) being partially attached or attachable to the stent component (2) along at least fixation lines (7', 7"), characterized in that said two fixation lines (7') are at least partially inclined with respect to an annular plane of said valve perpendicular to a flow direction (A) through the stent-valve (1) and wherein the third fixation line (7") runs parallel with respect to said plane.

42 Claims, 4 Drawing Sheets

(52) U.S. Cl.
CPC ............... *A61F 2210/0014* (2013.01); *A61F 2210/0057* (2013.01); *A61F 2220/0075* (2013.01); *A61F 2230/0008* (2013.01); *A61F 2230/0034* (2013.01); *A61F 2250/001* (2013.01); *A61F 2250/0006* (2013.01); *A61F 2250/0029* (2013.01); *A61F 2250/0036* (2013.01); *A61F 2250/0037* (2013.01); *A61F 2250/0039* (2013.01); *A61F 2250/0069* (2013.01); *A61F 2250/0098* (2013.01)

(56) References Cited

U.S. PATENT DOCUMENTS

| | | | |
|---|---|---|---|
| 5,258,023 | A | 11/1993 | Reger |
| 5,358,518 | A * | 10/1994 | Camilli ............ A61F 2/2403 137/521 |
| 8,795,354 | B2 | 8/2014 | Benichou et al. |
| 2004/0210303 | A1 | 10/2004 | Sedransk |
| 2006/0259135 | A1 | 11/2006 | Navia |
| 2007/0050021 | A1 | 3/2007 | Johnson |
| 2007/0288086 | A1 | 12/2007 | Kalmann et al. |
| 2008/0288055 | A1 | 11/2008 | Paul |
| 2009/0105813 | A1 | 4/2009 | Chambers |
| 2009/0132037 | A1 * | 5/2009 | Hoffman ............ A61F 2/2418 623/2.38 |
| 2009/0254176 | A1 * | 10/2009 | Butera ............ A61F 2/2418 623/1.24 |
| 2009/0281618 | A1 | 11/2009 | Hill et al. |
| 2010/0082094 | A1 | 4/2010 | Quadri et al. |
| 2010/0114307 | A1 * | 5/2010 | Agnew ............ A61F 2/2412 623/2.12 |
| 2010/0152835 | A1 | 6/2010 | Orr |
| 2011/0208297 | A1 | 8/2011 | Tuval |
| 2011/0319989 | A1 | 12/2011 | Lane |
| 2012/0197388 | A1 | 8/2012 | Khairkhahan |
| 2015/0088248 | A1 | 3/2015 | Scorsin et al. |

FOREIGN PATENT DOCUMENTS

| | | |
|---|---|---|
| CN | 102083391 | 6/2011 |
| CN | 102791223 A | 11/2012 |
| EP | 0183904 A2 | 6/1986 |
| EP | 1893132 | 3/2011 |
| EP | 0532678 B1 | 5/2016 |
| UA | 27373 C2 | 8/1992 |
| WO | WO 2003037227 | 5/2003 |
| WO | WO 2004093726 | 11/2004 |
| WO | WO 2007024755 | 3/2007 |
| WO | WO 2008/028569 | 3/2008 |
| WO | WO 2008/144476 A1 | 11/2008 |
| WO | WO 2009/052340 A1 | 4/2009 |
| WO | WO 2009/106545 | 9/2009 |
| WO | WO 2009132187 A1 | 10/2009 |
| WO | WO 2012/040643 A2 | 3/2012 |
| WO | WO 2013/160439 A1 | 10/2013 |
| WO | WO 2012/063228 | 9/2015 |
| WO | WO 2015/135883 | 9/2015 |

OTHER PUBLICATIONS

Definition of Line, Math Open Reference, pp. 1-3, date accessed Nov. 10, 2018.*
Chinese 1st Office Action & Translation dated May 3, 2017 for counterpart CN 201480027310.0.
International Search Report (ISR) dated Jun. 3, 2015 of parent case PCT/EP2015/054057.
Written Opinion of the International Search Authority (WOSA) dated Jun. 3, 2015 of parent case PCT/EP2015/054057.
Carpentier A., "Cardiac valve surgery—the french correction", Journal of thoracic and cardiovascular surgery, vol. 86, No. 3, 1986, p. 323-337, XP009166329 (ISSN 0022-5223).
Perier P. et al., Toward a new paradigm for the reconstruction of posterior leaflet prolapse; midterm results of the Respect Rather Than Resct approach, The annals of thoracic surgery, elsevier, us, vol. 86, No. 3, Sep. 2008, p. 718-725, XP024339074 (ISSN 0003-4975).
Office Action dated Jun. 4, 2018 for a related case from the USPTO with the U.S. Appl. No. 14/396,254 (published as US2015/0088248).
Butany J. and Collins M.J. Analysis of prosthetic cardiac devices: a guide for the practicing pathologist. J. Clin Pathol, Dec. 31, 2005. vol. 58, pp. 113-124.

* cited by examiner

CARDIAC STENT-VALVE AND DELIVERY DEVICE FOR SUCH A VALVE

CROSS REFERENCE TO RELATED APPLICATIONS

The present application is a U.S. national stage application of PCT/EP2015/054057 filed on Feb. 26, 2015, and claims foreign priority to European patent application EP 14305355.1 filed on Mar. 11, 2014, the contents of these two documents being herewith incorporated by reference in their entirety.

FIELD OF INVENTION

The invention is directed to expandable stent-valves and a delivery device for expandable stent-valves. It more precisely relates to cardiac stent-valves which include a single leaflet.

STATE OF THE ART

The replacement of cardiac valves with prostheses is a complex operation. The replacement is often carried out by an open heart surgery. Such an operation requires the opening of the chest, as well as the arrest of the patient's heart.

U.S. Pat. No. 4,759,758 suggests a mitral stent-valve comprising a stent and a single flap. The flap is sewn to a cutaway section of the stent by its lower edges to sewing holes extending along downwardly curving edges of the stent.

The stent-valve disclosed in U.S. Pat. No. 4,759,758 is a surgical stent-valve and is stitched to an annulus of the heart in an open heart surgery. An open heart surgery is a major procedure bearing the risk of surgical compliances such as e.g. infections.

During the last years, minimally invasive systems have been established to percutaneously deliver a stent prosthesis by catheter.

Stents to be delivered by catheter have to be crimped in order to be mounted on or into the catheter. Upon arriving at an implantation site, the stent is released and expands either through self-expansion or with the aid of auxiliary means such as balloons or wires.

WO 2009/106545 suggests using stents having finger like elements providing a radially acting tension force on the vascular wall. The tension force of the finger like elements anchors the stent.

Another possibility to anchor stents depends on an outer shape of the stent permitting a form fit anchoring at the native anatomy. EP 1 893 132 suggests a stent with an asymmetrical hourglass shape, wherein the portion with the larger diameter provides an anchoring of the stent through form fit. WO 2008/028569 suggests providing a round orifice for securing the stent valve through form fit.

WO 2012/063228 proposes a solution with a support structure and an anchoring member. The anchoring member is separate from the support structure and comprises for example a ring. The anchoring member co-operates with the peripheral wall of the support structure, extending around it so as to lock the valve leaflets of the cardiovascular valve between the anchoring member and the peripheral wall of the support structure.

However, a construction as described in WO 2012/063228 is complicated as there are two separate members which have to be connected inside the body. The combination has to be very accurate to provide a reliable anchoring.

Hence, there is a need for stents which avoid the disadvantage of the known state of the art. In particular, there is a need for stents which provide a reliable anchoring system with a simple and efficient construction and which are easy to use and which do not damage surrounding tissue.

DESCRIPTION OF THE INVENTION

Herein, the invention is mostly described for mitral stent-valves having only one leaflet. It is to be understood that the invention is also usable for other cardiac stent-valves.

The problem is solved with a stent-valve according to the independent claims of the present invention, in particular with an expandable, preferably a self-expandable, stent-valve. The stent-valve comprises a stent component and a valve component. The stent component comprises an inflow end and an outflow end and a wall between the inflow and the outflow end. The valve component comprises a single leaflet. The leaflet is partially attached or attachable to the stent component along its periphery. This partial attachment is defined along at least three fixations lines or, expressed differently, along a line defined by at least three sections. According to the invention, two fixation lines are at least partially inclined with respect to an annular plane of the valve perpendicular to a flow direction through the stent valve. The third fixation lines runs parallel to said plane. The inclination is preferably such that a free edge of the leaflet is closer to the outflow end than an edge of the leaflet fixed to the stent component at a level of the annular plane.

The two inclined fixation lines are preferably inclined in a range between about 5° and 50°, more preferably in a range of about 25° and 40°, preferably about 35° with respect to the annular plane.

The expandable stent-valve is either a self-expandable stent-valve or a stent-valve expandable with the aid of an expansion means. Such an expansion means might e.g. be a balloon.

The flow direction through the stent-valve is the general direction of the fluid flowing through the stent-valve, i.e. blood. The flow direction is basically parallel to a longitudinal axis of the stent-valve.

The leaflet might be directly attached to the stent component or indirectly. Indirect attachment means, that the leaflet is attached to means such as a skirt, which is itself attached to the stent component. The leaflet is preferably attached with stitches. Alternatively, the leaflet might be attached with clamps, staples or glue.

The attachment to the stent along the fixation lines is preferably a continuous fixation along the lines, e.g. a continuous suture. With a continuous attachment along the lines, the risk of paravalvular leakage is minimized compared to attachment with fixed and non-fixed attachment regions.

The leaflet preferably comprises and preferably is made of pericardium. Alternatively the leaflet might comprise or be made of other biological or synthetic biocompatible material.

As mentioned previously the leaflet is arranged such that two fixation lines are inclined with respect to a plane perpendicular to the flow direction through the stent-valve. The third line is preferably positioned between said two lines and is fixed substantially parallel or parallel to the perpendicular plane.

Alternatively, the inclined portions almost meet each other in one point, the so called saddle-horn. Hence, the third fixation line is reduced to a very small length.

One peripheral section between the two inclined fixation lines is not forming a part of the fixation lines and hence is not fixed to the stent component. This section is also referred to as the free edge of the leaflet.

The leaflet is movable between an open position wherein the free edge is distanced from the wall, allowing blood to pass the stent-valve and a closed position, blocking a reverse flow of the blood.

Mitral valves are open about 70-80% of their time. The stent-valve arrangement of the present invention stays open at rest when implanted in the mitral annulus. The leaflet closes because of systolic pressure during systole. When leaflets are arranged in a plane perpendicular to the flow direction as e.g. in trileaflet bioprosthetic valves, the stent-valve is pushed towards the left atrium with a resulting force vector is perpendicular to the annular plane. However, with a leaflet being attached according to the present invention, i.e., inclined with respect to the flow direction, a resultant vector of the systolic pressure pushes the leaflet radially towards the wall of the stent component. Therewith, when the leaflet closes it automatically prevents paravalvular leakage. Furthermore, the stent-component is pressed against the annulus tissue through the radially pressure of the leaflet towards the wall of the stent component and thus aids in anchoring of the stent-valve. The leaflet is preferably inclined in such a way that the stent-component is mainly pressed against the posterior ventricular wall.

The valve according to the invention provides further advantages. When the valve is open the main flow is oriented in an oblique direction with respect to the valve plane. The main flow direction is more preferably oriented towards the posterior wall of the left ventricle. This flow pattern has been described by several opinion leaders as the most physiologic and most suitable for a mitral valve prosthesis. In fact this oblique flow direction allows a better filling of the left ventricle and a less turbulent ejection of the blood towards the aorta.

The stent-valve preferably comprises a tissue support covering at least partly the inner surface of the stent. The tissue support helps to avoid paravalvular leakage. Other known means for reducing paravalvular leakage such as sealing gaskets may be possible. With a tissue support, the blood might not flow, or at least much less, around the leaflet on the outside of the stent-valve.

The wall of the stent component preferably comprises struts, which are preferably arranged basically in a zig-zag structure. The zig-zag structure of the struts form cells, preferably, diamond shaped cells.

Preferably, the struts have a diameter of about several millimetres. They are formed of a biocompatible material such as biocompatible metals or metal alloys, e.g. Nitinol.

An arrangement of the wall with struts having basically a zig-zag structure provides a stable stent needing little material. Furthermore, such an arrangement is well crimpable for delivery because of the free space between the struts.

The wall made of struts will be pushed radially outwardly towards the annulus and the ventricular, preferably the posterior ventricular, wall during systole by the systolic pressure acting on the inclined leaflet. An arrangement with struts aids in anchoring as the friction is bigger in uneven, non-smooth surfaces. The wall with struts and free space in between provides such an uneven surface.

Preferably, the stent component is generally in a D-shape. Herein, a D-shape is meant to cover shapes comprising two sections, one of which is bent in about circular manner whereas the other part is substantially straight or bent to a less degree on either side, respectively. Hence, e.g. an oval shape is meant to be covered by the term D-shape.

The mitral annulus is generally in a D-shape. Hence, a stent component with generally a D-shape suits the mitral annulus better than e.g. a circular shape. With a D-shape the stent-valve is basically not deformed upon implantation. As a deformation might result in malfunction of the stent-valve because of e.g. inaccurate closure of the leaflet a D-shape is the preferred construction.

Alternatively it might be possible to provide a stent component with generally a circular shape. If the stent-valve is used in other valves, e.g. in the aortic annulus, a generally circular shape might be preferable.

In a preferred embodiment of a mitral stent-valve, a distance between the inflow and the outflow end is shorter at an anterior side than at a posterior side of the stent component.

The terms anterior and posterior side of the stent component refer to the position of the portions upon implantation. Hence, a anterior side is in the region of the anterior portion of the annulus when implanted and the posterior side in the region of the posterior portion of the annuls.

The anterior portion of the mitral annulus is located near the aortic annulus. By providing a stent component with a shorter anterior side, the anterior side will extend only little into the ventricle on the anterior side. Therewith, the stent-valve will interfere less with the flow of the blood through the aortic annulus than a stent component extending further into the ventricle. The longer side might e.g. be achieved with bigger cells and/or a further row of cells on the longer side.

Preferably, the leaflet is attached at the anterior side and the lateral sides of the stent component, such that the inclined fixation lines are arranged at the lateral sides. The free edge is therefore preferably arranged at the posterior side.

Analogous to the anterior and the posterior portions, lateral sides refer to the position of the sides upon implantation. The fixation line at the anterior side is preferably generally parallel to the plane perpendicular to the flow direction through the stent.

Alternatively, the inclined fixation lines are arranged at the lateral sides and at the anterior side. The inclined fixation lines meet at a contact point at the anterior side. The free edge is therefore also preferably arranged at the posterior side.

In such arrangements, the stent is pressed radially against the posterior portion of the ventricular wall and mitral annulus during systole. As described above, the anterior portion is located near the aortic annulus. Therefore, pressure of the stent against the posterior portion is favoured because of less interference with the blood flow through the aortic annulus. The aortic annulus is not deformed when the stent is pressed against the posterior portion of the annulus.

Furthermore, in case of the posterior wall being longer than the anterior wall, the surface to be pressed against the annulus is enlarged with the described arrangement. This further increases the anchoring of the stent-valve.

The anterior wall is preferably barely anchored to the mitral annulus. The anterior mitral annulus is near the aortic valve orifice. There is no ventricular wall at the level of the anterior mitral annulus. With the arrangement pressing the stent against the posterior ventricular wall, the anterior side does not have to be anchored as firmly as the posterior side. By pressing the stent against the posterior ventricular wall, the aortic valve is preferably not obstructed and consequently the ventricular flow is not disrupted.

Preferably, the leaflet is arranged such as the at least one leaflet is arranged such as anterior side and a free edge of the valve leaflet each have a length of about 30 to 40% of the annular circumference of the stent valve and inclined portions at the lateral sides have a length in the range of between 10 and 20%, preferably 15% of the annular circumference.

In a preferred embodiment, the stent-valve further comprises at least two, tissue support. The at least two tissue supports are attached to the stent component, preferably attached to an inner surface of the stent component. The at least two tissue supports preferably covers at least a part of the inner surface of the stent component.

At least two tissue supports in the context of this application means that there are at least two sections. At least two tissue supports does include also two integrally formed sections (e.g. a section covering an inner surface of an inflow end of the stent and attached to second section covering an inner surface of an outflow end of the stent, connected sections), as well as separated, not connected sections.

The tissue supports preferably comprise and preferably are made of the same material as the leaflet, i.e. preferably pericardium. A tissue support(s) attached to the inner surface of the stent component allows a less disturbed flow of the blood through the stent as the blood is not in direct contact with uneven surface such as e.g. the struts. Uneven surfaces might result in turbulences.

Alternatively the tissue supports are made other material, e.g. of synthetic biocompatible material.

Preferably, at least one tissue support comprises an attachment area. At least a section of the attachment area preferably extends essentially inwardly from the inner surface. The at least one leaflet is attached to the tissue support at the section of the attachment area such that the leaflet is arranged between the attachment area of the at least two tissue supports or integrally formed with one tissue support and attached to the second tissue support at the section of the attachment area.

The tissue support may extend along the entire circumference or only along parts of the circumference of the stent or the annulus. The attachment area may circumferentially extend along the complete tissue support or only along parts of the tissue support.

Preferably, the prosthetic valve further comprises a stent component. The at least two tissue supports are attached to an inner surface of the stent component and at least partly cover the inner surface of the stent component.

The tissue supports may be arranged such that the entire length of the stent is covered with tissue support or such that only parts of the length of the stent are covered with tissue support.

The leaflet is preferably not directly and fixedly attached to the valvular stent but indirectly via one or more tissue supports. The attachment of the functional leaflet as well as the whole functional leaflet itself is completely inside the stent. Therefore, the leaflet is not bending over any struts or the like, e.g., during systo-diastolic opening. Therewith, the stress occurring along such bending lines are avoided.

The inclined fixation lines are preferably attached to the tissue supports independently of the arrangement of the struts of the stent component.

By attaching the leaflet to the tissue supports instead of directly to the stent component, the orientation of the attachment lines is not dependent on the shape of the stent component, i.e. the orientation of the struts, which provide an attachment site. The attachment line can therefore be oriented independently of the strut geometry.

The stent component preferably comprises at least one, preferably three, atrial extensions.

Atrial extensions as described herein refers to portions of the stent which are arranged generally perpendicular to a flow direction of the blood through the stent and have a bigger cell size than basically the rest of the wall. The atrial extensions are placed at the inflow end of the stent-valve. The atrial extensions therefore protrude outwardly from the stent-valve and aid in anchoring and stabilization of stent valve in the annulus as they are in contact with the heart wall when implanted.

The atrial extensions are preferably arranged all around the circumference of the inflow end of the stent-valve. The atrial extensions are arranged similar to petals in a flower. Therewith, the aortic annulus is basically not deformed and generally no interference with the blood flow through the aortic annulus occurs.

The outermost zig-zag forming struts on the inflow end might also be perpendicularly bent radially outwardly circumferentially on the stent component. Therewith, also an anchoring on the atrial side is enhanced. Because of the preferred relatively small cell size on the inflow end, there occurs basically no interference with the aortic blood flow.

In case of walls formed by struts, cells formed by the struts have preferably different sizes at least in the outflow region and the inflow region.

Preferably, the outflow end comprises bigger cells than the inflow end. Parts with bigger cells are generally more flexible than parts with smaller cells. The zig-zag lines might also vary in size such as to produce cells with different sizes in one row as e.g. bigger cells on the posterior side than the anterior side in one row. Therewith, different length of the sides of the stent component might be achieved. The atrial flaps are preferably also constructed out of bigger zig-zags lines in the outermost zig-zag in the inflow region.

The wall of the stent component preferably comprises decoupling elements to reduce stress during systo-diastolic stent flaring. The decoupling elements are preferably in a S-shape.

An S-shape as describe herein is to be meant to encompass shapes achieved with bars connected with alternate bendings, such as e.g. a Z-shapes or serpentine shapes, i.e. multiple S- or Z-shapes.

The decoupling elements are preferably arranged between zig-zag structures having different sizes. The decoupling elements connect at least some of the cells formed by the struts. Preferably, the decoupling elements connect some cells of the outermost row of cells of the inflow region with cells in an adjacent row in flow direction.

It has been shown that the decoupling elements can aid in grabbing the native anterior leaflet such as to pull-up the leaflet towards the mitral annulus. Therewith, the native leaflet does not obstruct the left ventricle outflow tract. The native leaflet might be completely entrapped by the decoupling elements.

The decoupling elements on the posterior side have the same effect but the native posterior leaflet remains pinched between the posterior cardiac wall and the stent-valve.

Preferably, the width of decoupling elements is reduced compared to the width of the struts.

In addition to the stress reduction, the decoupling elements provide more flexibility to the stent-valve.

Further additionally, the decoupling elements help to keep the stent-valve in place during ventricular systole.

Preferably at least one of the inflow end and the outflow end, preferably both, are flared outwardly with respect to a central axis parallel to the flow direction.

The inflow end is preferably flared about 20° to 50, more preferably about 30°, with respect to the flow direction and the outflow end is preferably flared about 7.5° up to 17.5°, more preferably about 10°, with respect to the flow direction.

The posterior side is preferably flared with a larger angle than the anterior side.

The anterior side is flared at the outflow end preferably about 7.5° to 20°, more preferably about 10°, with respect to the axis and flared at the inflow end preferably about 15° to 30°, more preferably about 20°, with respect to the axis whereas the posterior side is flared at the outflow end, preferably about 7.5° to 17.5°, more preferably about 10°, with respect to the axis and at the inflow end about 20° to 50°, more preferably about 30°, with respect to the axis. The asymmetric flare might be present in combination with the various prosthesis of the invention described herein.

In a further alternative embodiment, the flares might be provided as curvilinear flares. Curvilinear flares mean that the flares are bent in a circular, convex manner with respect to the axis so that the flare bends outwardly in an intermediate region and at least slightly inwardly in the area closer to the inflow end or the outflow end, respectively, with respect to the axis. The curvilinear flares might be present in combination with the various prostheses of the invention described herein.

The flares provide a force of the support structure on the atrio-ventricular junction and surrounding tissues of the posterior ventricular wall, which keeps the fixation of the support structure in the annulus. A smaller flare at the outflow end of the anterior portion than on the posterior portion helps minimizing the risk of obstructing the aortic outflow tract.

The stent-valve preferably comprises markers, e.g. radio opaque markers which form positioning means. The means aid in axially and/or rotationally positioning of the stent upon implantation with a catheter. The positioning means might comprise material visible on an ultrasonic imaging of the operation. The markers might also be arranged on a delivery device onto which the stent-valve is mounted.

The present invention further relates to a delivery system comprising a delivery device and a stent-valve according to one of the above described embodiments.

Further aspects of the invention are described with reference to the following schematic figures. The figures schematically show:

FIG. 1 shows a view on a stent valve 1 seen from the outflow end 5. The stent valve comprises a stent component 2 and a valve component 3. The stent component 2 comprises an inflow end 4 and an outflow end 5. Between the ends 4, 5, the stent component 2 comprises a wall formed by struts 8 made of Nitinol. The struts 8 are constructed in a zig-zag shape forming cells with different sizes. S-shaped decoupling elements 11 are connecting some of the cells in a flow direction A. The decoupling elements 11 have a reduced diameter as compared to the struts 8. The reduced diameter and the S-shape of the decoupling elements 11 provide a reduction of stress during the stent-valve 1 flaring. Therewith a better conformability of the stent-valve 1 is achieved.

Figure 1:
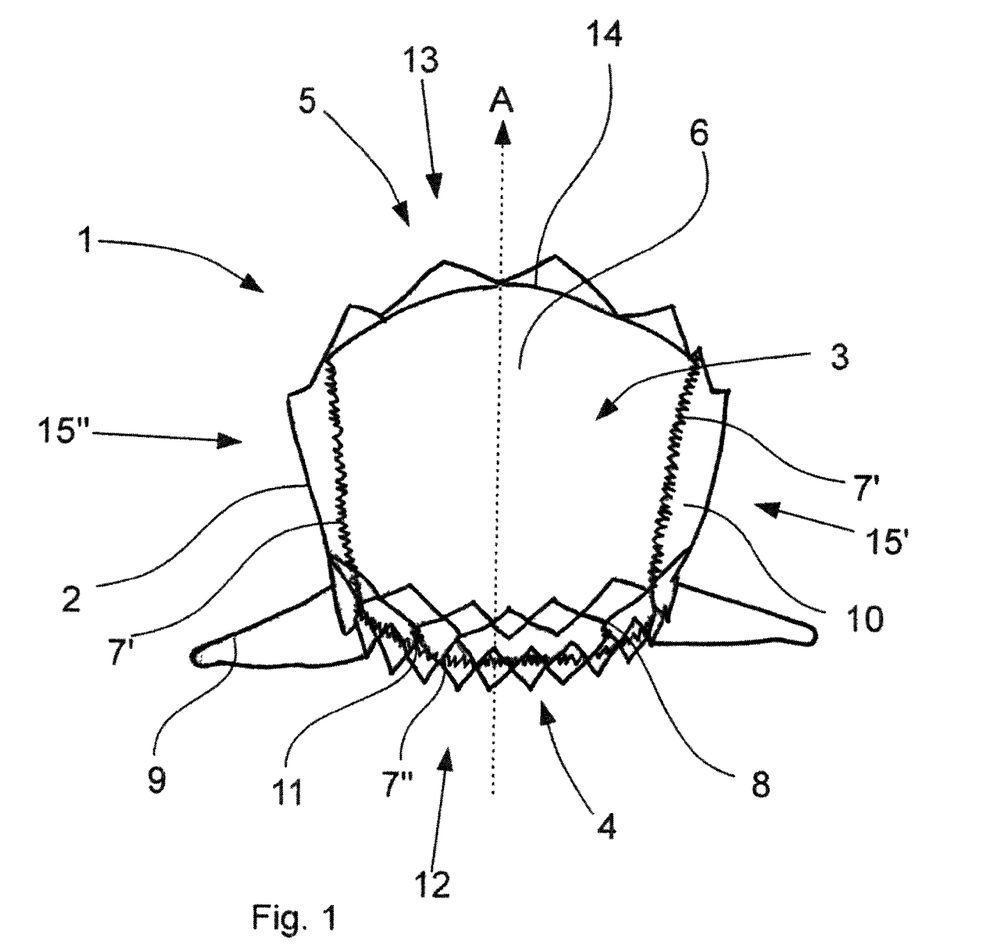
FIG. 1: a perspective view of a stent-valve according to the invention, seen from an outflow end FIGS. 2a, b: a side view of a stent-valve according to FIG. 1 in an open and closed position

The stent component 2 further comprises three atrial extensions 9 on the inflow end 4 (only two shown in FIG. 1, the third is hidden). The atrial extensions 9 are arranged basically perpendicularly to the flow direction A through the stent-valve 1. As the atrial extensions 9 protrude outwardly from the stent-valve 1, the atrial extensions 9 contact the atrial heart wall when implanted and aid in anchoring and stabilization of the stent-valve 1.

The valve component 3 comprises one leaflet 6 attached to tissue supports 10 with stitches along fixation lines 7', 7". The leaflet and the tissue supports are made of pericardium. The stitches on an anterior side 12 attach the tissue support 10 to the stent component 2 at the same time as attaching the leaflet 6 to the tissue supports 10 and therefore to the stent component 2. On the lateral sides 15', 15" the fixation line 7' is inclined with respect to a plane perpendicular to the flow axis A through the stent-valve 1. The fixation lines 7' on the lateral sides 15', 15" are inclined starting from the fixation line 7" running parallel to said plane. The fixation line 7" on the anterior side 12 is arranged near the inflow end 4 of the stent-valve 1. The fixation lines 7' run from the fixation line 7" under an angle towards the outflow end 5 of the stent-valve 1. A free edge 14 of the leaflet 6 is in contact with the wall on a posterior side 13 of the stent component 2 in the shown, closed position (see also FIG. 2b).

The leaflet 6 is in an open position during diastole and at rest. During systole, the blood is pumped from the left ventricle into the aorta. The pressed blood also acts on the leaflet 6 and therewith closes the leaflet 6. Because of the inclined position of the leaflet 6, the force also pushes the leaflet 6 radially against the posterior wall (see FIG. 3). Through the pressure, the stent-valve 1 itself is pushed against the posterior annulus wall and therewith aids in anchoring of the stent-valve 1 in the mitral annulus and in the surrounding ventricular wall.

Figure 2A:
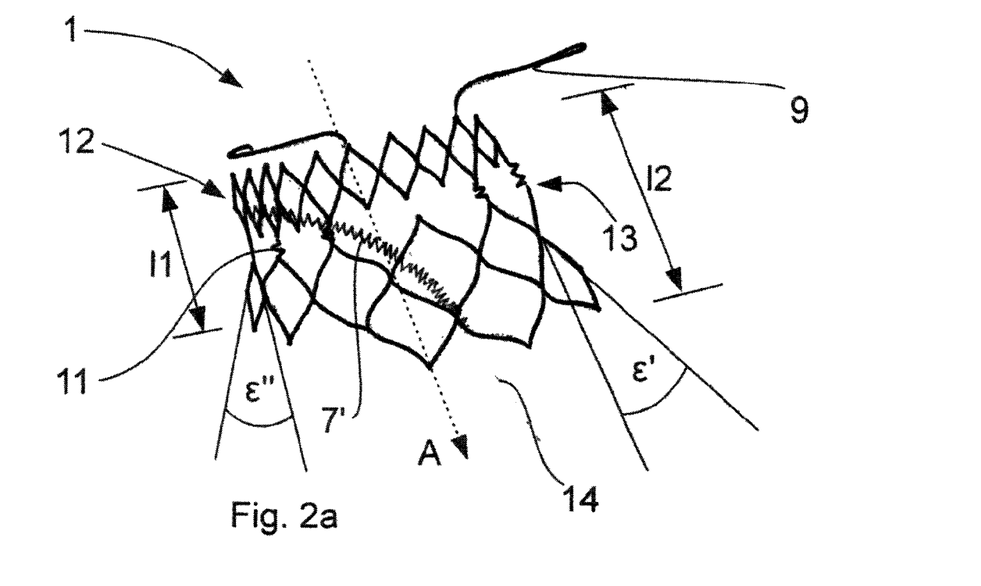

FIGS. 2a, b show a side view of the stent-valve 1. FIG. 2a shows the stent-valve 1 in an open position, FIG. 2b in a closed position.

Figure 2B:
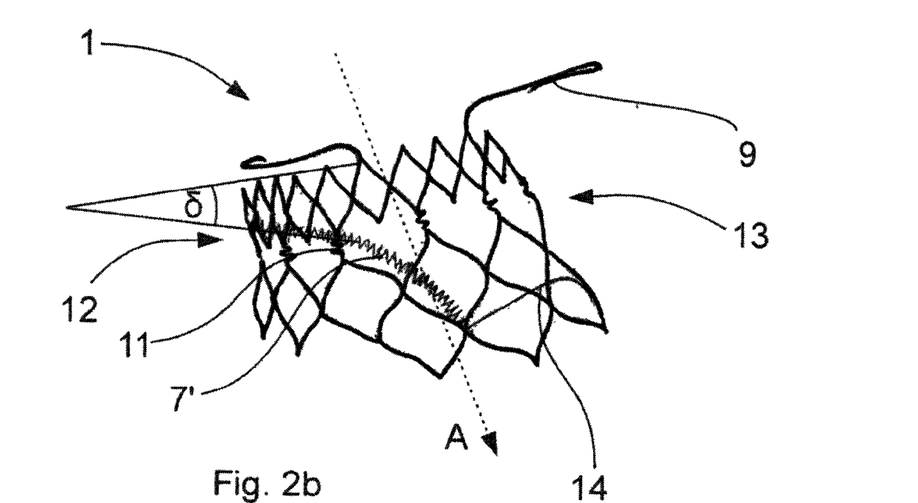

The fixation lines 7' run at an angle δ of between 20° and 50°, preferably around 35° with respect to the plane perpendicular to the flow direction A. The angle δ may vary over the length of the fixation lines 7' starting with a small angle δ 20° at the fixation line 7" to a larger angle δ 50° towards the outflow end 5, or vice versa.

The walls on the outflow end 5 of the stent component 2 are flared with respect to the flow direction A. The walls of the posterior side 13 are flared with an angle ε' of about 20° and the walls of the anterior side 12 with an angle ε" of about 18°

The anterior side 12 has a length l1 of about 15 to 17 mm and the posterior side 13 has a longer length l2 of about 32 mm. The length of the valve is about 30 to 45 mm, preferably about 34 mm.

In the open position shown in FIG. 2a, the free edge 14 of the leaflet is not in contact with the posterior wall of the stent component 2. The free edge 14 of the leaflet 6 is directed from the inclined fixation lines 7' into the left atrium in a stress-relieved state. The blood can flow in the flow direction A from the left ventricle through the stent-valve 1 into the left atrium of the heart in the open position.

In the closed position shown in FIG. 2b, the systolic pressure has pushed the free edge 14 of the leaflet against the posterior wall. The closed position of the leaflet 6 prevents a backflow of the blood from the left atrium into the left ventricle. By pushing the leaflet 6 onto the posterior wall, a force B (see FIG. 3) in posterior direction is acting on the stent-valve 1. The stent-valve 1 is therewith pushed in posterior direction aiding in anchoring of the stent-valve 1 during systole. The kinetic force of the left ventricle helps anchoring the stent-valve in the mitral position.

Figure 3:
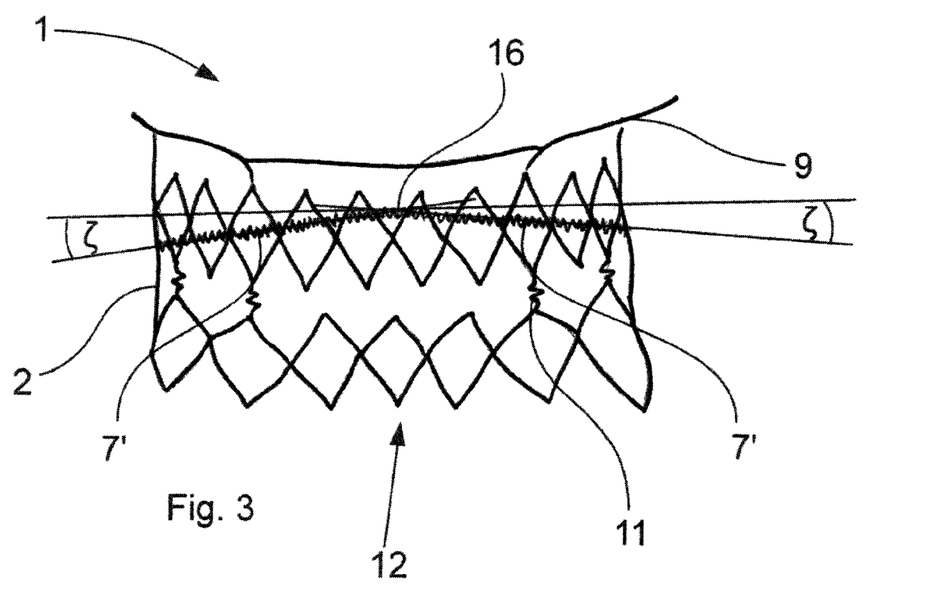
FIG. 3: a perspective view of an alternative stent-valve according to the invention, seen from an anterior side

FIG. 3 shows an alternative stent-valve 1 according to the invention seen from an anterior side 12. The stent-valve comprises a stent component 2 and a valve component 3. The valve component 3 is attached to the stent component 2 with sutures along inclined fixation lines 7'. The inclined fixation lines are arranged at lateral sides 15', 15" and at the anterior side 2. The inclined fixation lines 7' meet on the anterior side 12 in a contacting point 16, a so called saddle-horn. From the saddle horn 16 the fixation lines 7' both incline with an angle of about 5 to 10°. The angle increases towards the outflow end to an angle of about 35° on the lateral sides 15', 15".

Figure 4:
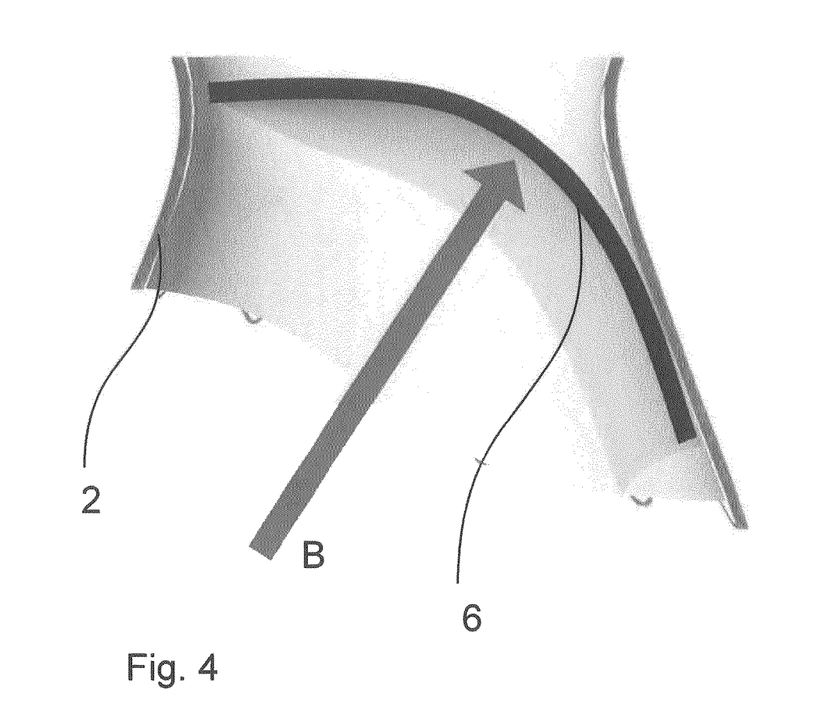
FIG. 4: the principle of systolic force acting on the leaflet in a stent-valve according to the invention

FIG. 4 shows the principle of the force B acting on the leaflet 6 and therewith on the stent-valve 1 during systole. The kinetic force during systole pushes the leaflet 6 against the posterior side 13. The leaflet 6 might not change the position over the whole length as shown in FIG. 3, as the inclined portions are at least partially attached to support tissues 10.

With an inclined leaflet 6 a larger coaptation is achieved. The coaptations is in minimum 10 mm in length. In mitral valves where the pressure is lower than in e.g. trileaflet prosthesis, a large coaptation surface is important to minimize paravalvular leakage.

Figure 5:
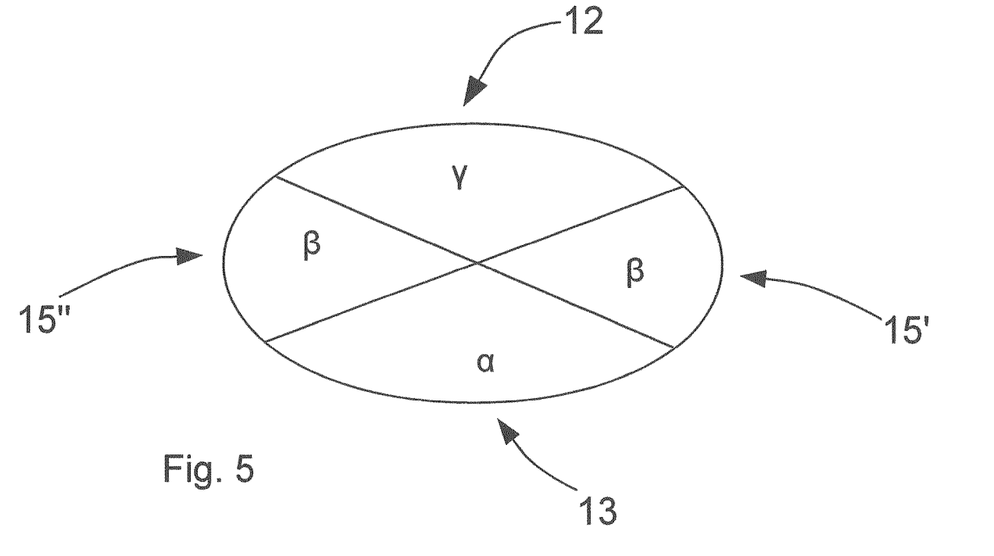
FIG. 5: circumferential dimensions of the stent-valve in a top view

FIG. 5 shows the circumferential dimensions of the stent-valve 1 in a top view. The fixation line 7" has a circumferential dimension γ on the anterior side 12 of about 30 to 40%. The fixation lines 7' on the lateral sides 15', 15" have a circumferential dimension β of about 10 to 20% each. The free edge 14 has a circumferential dimension α on the posterior side 13 of about 30 to 40%. The length of the fixation lines 7' is about 25 mm.

The invention claimed is:

1. A cardiac stent-valve comprising:
   a stent component; and
   a single leaflet forming a valve component,
   wherein the stent component includes an inflow end, an outflow end, and a wall between the inflow end and the outflow end,
   wherein a periphery of the single leaflet is partially attached or configured to be attached to the stent component along at least three fixation lines, two fixation lines of the at least three fixation lines being inclined with respect to an annular plane of the valve component, the annular plane being perpendicular to a flow direction of the cardiac stent-valve,
   wherein the third fixation line of the at least three fixation lines is arranged substantially parallel to the annular plane,
   wherein the single leaflet is arranged such that an anterior side and a free edge of the single leaflet each have a length in a range of approximately 30% to 40% of an annular circumference of the stent component, and
   wherein inclined portions at lateral sides of the single leaflet have a length in a range of approximately 10% and 20% of the annular circumference of the stent component.

2. The cardiac stent-valve according to claim 1, wherein the wall includes struts that are arranged in a zig-zag structure.

3. The cardiac stent-valve according to claim 2, wherein cells formed by the struts have different sizes in an area of the outflow end and in an area of the inflow end.

4. The cardiac stent-valve according to claim 1, wherein the stent component is arranged in a D-shape.

5. The cardiac stent-valve according to claim 1, wherein a distance between the inflow end and the outflow end is shorter at an anterior side than at a posterior side of the stent component.

6. The cardiac stent-valve according to claim 1, wherein the single leaflet is attached at an anterior side and lateral sides of the stent component, such that the two fixation lines are arranged at the lateral sides.

7. The cardiac stent-valve according to claim 1, further comprising:
   two tissue supports attached to the stent component and covering at least a part of an inner surface of the stent component.

8. The cardiac stent-valve according to claim 7, wherein the single leaflet is attached to the two tissue supports.

9. The cardiac stent-valve according to claim 1, wherein the stent component further includes a plurality of atrial extensions.

10. The cardiac stent-valve according to claim 1, wherein the wall comprises:
    decoupling elements to reduce stress during stent flaring, the decoupling elements having an S-shape.

11. The cardiac stent-valve according to claim 10, wherein the decoupling elements are configured to grab a native leaflet and to pull the native leaflet towards a mitral annulus.

12. The cardiac stent-valve according to claim 1, wherein at least one of the inflow end and the outflow end are flared outwardly with respect to a central axis parallel to the flow direction.

13. The cardiac stent-valve according to claim 12, wherein a posterior side of the stent component is flared with a larger angle than an anterior side of the stent component.

14. The cardiac stent-valve according to claim 1, forming a mitral stent-valve.

15. The cardiac stent-valve according to claim 1, wherein the two fixation lines are inclined in a range between approximately 25° and 40° with respect to the annular plane.

16. The cardiac stent-valve according to claim 1, wherein the two fixation lines are inclined by approximately 35° with respect to the annular plane.

17. The cardiac stent-valve according to claim 1, wherein the single leaflet is arranged inside of the stent component, and is partially attached or configured to be attached to an inner side of the wall of the stent component.

18. The cardiac stent-valve according to claim 1, wherein the stent component has a tubular shape.

19. The cardiac stent-valve according to claim 1, wherein the two fixation lines are inclined in a range between approximately 5° and 50° with respect to the annular plane.

20. The cardiac stent-valve according to claim 1, wherein the at least three fixation lines form a continuous fixation.

21. A delivery system comprising:
    a delivery device; and
    a cardiac stent-valve according to claim 1.

22. A cardiac stent-valve comprising:
    a stent component; and
    a valve component, wherein the stent component includes an inflow end, an outflow end, and a wall between the inflow end and the outflow end,
wherein the valve component is made of a single leaflet, a periphery of the single leaflet being partially attached or configured to be attached to the stent component along at least three fixation lines, two fixation lines of the at least three fixation lines being at least partially inclined with respect to an annular plane of the valve component, the annular plane being perpendicular to a flow direction of the cardiac stent-valve,
wherein the third fixation line of the at least three fixation lines is arranged substantially parallel to the annular plane, and
wherein the stent component is arranged in a D-shape.

23. The cardiac stent-valve of claim 22, wherein the two fixation lines are inclined in a range between approximately 5° and 50° with respect to the annular plane.

24. The cardiac stent-valve of claim 22, wherein the wall comprises:
decoupling elements to reduce stress during stent flaring.

25. A delivery system comprising:
a delivery device; and
a cardiac stent-valve according to claim 22.

26. The cardiac stent-valve according to claim 22, wherein the at least three fixation lines form a continuous fixation.

27. A cardiac stent-valve comprising:
a stent component; and
a single leaflet forming a valve component,
wherein the stent component includes an inflow end, an outflow end, and a wall between the inflow end and the outflow end,
wherein a periphery of the single leaflet is partially attached or configured to be attached to the stent component along at least three fixation lines, two fixation lines of the at least three fixation lines being inclined with respect to an annular plane of the valve component, the annular plane being perpendicular to a flow direction of the cardiac stent-valve,
wherein the third fixation line of the at least three fixation lines is arranged substantially parallel to the annular plane,
wherein the wall of the stent component includes struts that are arranged in a zig-zag structure; and
wherein cells formed by the struts have different sizes in an area of the outflow end and in an area of the inflow end.

28. The cardiac stent-valve according to claim 27, wherein the at least three fixation lines form a continuous fixation.

29. The cardiac stent-valve according to claim 27, wherein the two fixation lines are inclined in a range between approximately 5° and 50° with respect to the annular plane.

30. A delivery system comprising:
a delivery device; and
a cardiac stent-valve according to claim 27.

31. A cardiac stent-valve comprising:
a stent component; and
a single leaflet forming a valve component,
wherein the stent component includes an inflow end, an outflow end, and a wall between the inflow end and the outflow end,
wherein a periphery of the single leaflet is partially attached or configured to be attached to the stent component along at least three fixation lines, two fixation lines of the at least three fixation lines being inclined with respect to an annular plane of the valve component, the annular plane being perpendicular to a flow direction of the cardiac stent-valve,
wherein the third fixation line of the at least three fixation lines is arranged substantially parallel to the annular plane,
wherein the wall of the stent component includes decoupling elements to reduce stress during stent flaring, the decoupling elements having an S-shape.

32. The cardiac stent-valve according to claim 31, wherein the at least three fixation lines form a continuous fixation.

33. The cardiac stent-valve according to claim 31, wherein the two fixation lines are inclined in a range between approximately 5° and 50° with respect to the annular plane.

34. A delivery system comprising:
a delivery device; and
a cardiac stent-valve according to claim 31.

35. A cardiac stent-valve comprising:
a stent component; and
a single leaflet forming a valve component,
wherein the stent component includes an inflow end, an outflow end, and a wall between the inflow end and the outflow end,
wherein a periphery of the single leaflet is partially attached or configured to be attached to the stent component along at least three fixation lines, two fixation lines of the at least three fixation lines being inclined with respect to an annular plane of the valve component, the annular plane being perpendicular to a flow direction of the cardiac stent-valve,
wherein the third fixation line of the at least three fixation lines is arranged substantially parallel to the annular plane,
wherein at least one of the inflow end and the outflow end are flared outwardly with respect to a central axis parallel to the flow direction, and
wherein a posterior side of the stent component is flared with a larger angle than an anterior side of the stent component.

36. The cardiac stent-valve according to claim 35, wherein the at least three fixation lines form a continuous fixation.

37. The cardiac stent-valve according to claim 35, wherein the two fixation lines are inclined in a range between approximately 5° and 50° with respect to the annular plane.

38. A delivery system comprising:
a delivery device; and
a cardiac stent-valve according to claim 35.

39. A cardiac stent-valve comprising:
a stent component; and
a single leaflet forming a valve component,
wherein the stent component includes an inflow end, an outflow end, and a wall between the inflow end and the outflow end,
wherein a periphery of the single leaflet being partially attached or configured to be attached to the stent component along at least three fixation lines, two fixation lines of the at least three fixation lines being at least partially inclined with respect to an annular plane of the valve component, the annular plane being perpendicular to a flow direction of the cardiac stent-valve, wherein the third fixation line of the at least three fixation lines is arranged substantially parallel to the annular plane, wherein the three fixation lines have a length in a range of approximately 50% to 80% of an annular circumference of the stent component, and wherein the two inclined fixation lines have a length in a range of approximately 10% to 20% of the annular circumference of the stent component, and the third fixation line has a length in a range of approximately 30% to 40% of the annular circumference of the stent component.

40. The cardiac stent-valve according to claim 39, wherein the at least three fixation lines form a continuous fixation.

41. The cardiac stent-valve according to claim 39, wherein the two fixation lines are inclined in a range between approximately 5° and 50° with respect to the annular plane.

42. A delivery system comprising:
a delivery device; and
a cardiac stent-valve according to claim 39.

* * * * *